United States Patent [19]

Garabedian

[11] Patent Number: Plant 7,148

[45] Date of Patent: Feb. 13, 1990

[54] PLUM TREE, "JAKE'S BEST"

[76] Inventor: John M. Garabedian, P.O. Box 7883, Fresno, Calif. 93747

[21] Appl. No.: 268,347

[22] Filed: Nov. 7, 1988

[51] Int. Cl.[4] ..... A01H 5/00

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of Plum Tree which is characterized as to novelty by a date of harvesting and shipment approximately May 27 through June 3 under the ecological conditions prevailing at Fresno, Calif. in the San Joaquin Valley of central California.

1 Drawing Sheet

BACKGROUND OF THE NEW VARIETY

The present invention relates to a new and distinct variety of Plum Tree which has been denominated varietally as "Jake's Best" and more particularly to such a plum tree which bears fruit which are somewhat closely similarly in their overall physical characteristics to the "Wuhl" Plum Tree (U.S. Plant Pat. No. 5,585) but which is distinguished therefrom and characterized principally as to novelty by producing fruit which are ripe for commercial harvesting and shipment approximately two or three weeks earlier than the fruit produced by the Wuhl Plum Tree and which further produces fruit that are semi-freestone by nature in contrast to the Wuhl Plum Tree which produces a clingstone fruit.

It has long been known that the marketability of plums can be influenced to some degree by numerous factors including its date of harvesting and shipment as well as its external appearance. The Jake's Best Plum Tree is noteworthy in producing an attractively colored, early season plum which is ripe for commercial harvesting and shipment from approximately the last week of May through June 3 in Fresno, Calif. and which has a commercially aesthetic appeal such as that presented by the Wuhl Plum Tree (U.S. Plant Pat. No. 5,585). The fruit produced by the subject variety is noteworthy in that it is somewhat similar in its overall physical characteristics to the fruit produced by the Wuhl Plum Tree but is distinguishable by being ripe for commercial harvesting and shipment approximately two weeks earlier than the Wuhl Plum Tree and is semi-freestone by nature.

ORIGIN AND ASEXUAL REPRODUCTION OF THE NEW VARIETY

The present variety of plum tree was discovered as an open pollinated seedling of unknown parentage growing within the cultivated area of Nursery No. 1, on applicant's Ranch No. 1, which is located at the corner of Kings Canyon and Fowler Avenues in Fresno, Fresno County, Calif. in 1980. The inventor, at that time, noted the novel characteristics of the instant variety of plum tree and marked the chance seedling for subsequent observation.

The first asexual reproduction of the present variety of plum tree occurred in 1981 when the inventor removed buds from the chance seedling and budded them into test trees which were then growing on the applicant's Ranch No. 1 located in Fresno, Calif. The test trees have been continually observed by the inventor and it has subsequently been determined that the budded test trees produce progeny which have identical characteristics to that observed in the original chance open pollinated seedling.

SUMMARY OF THE NEW VARIETY

The Jake's Best Plum Tree is characterized principally as to novelty by producing a good quality, early season plum. The present variety of plum tree bears a plum which is ripe for harvesting and shipment approximately two weeks earlier than the Wulh Plum Tree (U.S. Plant Pat. No. 5,585) with which it is most closely similar in its external appearance but which is distinguished therefrom and characterized principally as to novelty by bearing semi-freestone fruit which are somewhat smaller than that produced by the Wuhl Plum Tree.

BRIEF DESCRIPTION OF THE DRAWINGS

The accompanying drawing is a color photograph of a characteristic twig bearing typical leaves, several mature fruit showing their external coloration sufficiently matured for harvesting and shipment, two fruit of the subject variety dissected in the axial plane to illustrate the flesh characteristics thereof and several stones, all of the subject variety.

DETAILED DESCRIPTION

Referring more specifically to the pomological details of this new and distinct variety of plum tree, the following has been observed under the ecological conditions prevailing at the orchard of the inventor which is located in Fresno, Calif. All major color code designations are by reference to the Dictionary of Color by Maerz and Paul, Second Edition, 1950. Common color names are also employed occasionally.

TREE

Generally:

*Size.*—Average as compared with other common plum cultivars.

*Vigor.*—Medium.

*Figure.*—Upright, open and tender. The tree can be adapted to a vase formed figure.

*Productivity.*—Productive.

*Regularity of bearing.*—Regular.

Trunk:

*Size.*—Average as compared with other common plum cultivars.
*Surface. texture.*—Shaggy.
Branches:
*Size.*—Medium.
*Surface texture.*—Shaggy.
*Color.*—Brown. This color is not particularly distinctive of the subject variety.
Lenticels:
*Numbers.*—Variable.
*Size.*—Small.

LEAVES

Size:
*Generally.*—Average.
*Average length.*—Approximately 8.6 cm.
*Average width.*—Approximately 4.1 cm.
Shape:
*Generally.*—Lanceolate and acutely pointed.
Thickness: Thin.
Surface texture: Glabrous.
Color:
*Upwardly disposed surfaces.*—Dark Green, (Plate 23, J-9 page 69).
*Downwardly disposed surfaces.*—Pale Green, (Plate 20, D-2, page 63).
Marginal form: Finely serrated.
Petiole:
*Average length.*—Approximately 17.2 mm.
*Thickness.*—Slender, approximately 1.4 mm.
Glands:
*Generally.*—Not evident.

FLOWER BUDS

Size:
*Generally.*—Small.
Length: Short.
Form: Pointed, free and tender.
Pubescent: Average, and occasionally light.
Flowers produced per node: Generally only two flowers per node were produced.

FLOWERS

Date of full bloom: In 1987, full bloom was observed on February 28.
Date of earliest bloom: In 1987, the date of earliest bloom was observed on February 23.
Date of bloom:
*Generally.*—Average as compared with other common varieties.
Size: Average.
Color: White.
Date of bloom as compared with other common plum varieties: The date of bloom is approximately the same as the Red Beaut Plum Tree (U.S. Plant Pat. No. 2,539) but appears somewhat slightly later than the Eldorado Plum Tree (unpatented) and earlier than the Salvador Black.

FRUIT

Maturity when described: Ripe for commercial harvesting and shipment approximately May 27 through June 3 and occasionally later, under the ecological conditions prevailing at Fresno, Calif.
Size:
*Generally.*—Average as compared with other common plum cultivars.
Uniformity: Uniform.
Average axial diameter: Approximately 39.7 mm.
Average diameter transverse in the suture plane: Approximately 46.9 mm.
Average diameter transverse and at right angles to the suture plane: Approximately 32.6 mm.
Form:
*Generally.*—Unsymmetrical with one cheek generally appearing slightly larger than the other cheek.
Suture: The suture appears as a distinct but shallow line which extends from the base to the apex. The suture appears to discontinue at the apex.
Ventral surface:
*Shape.*—Rounded slightly.
Stem cavity:
*Shape.*—Flaring and rounded.
*Depth.*—Approximately 10.6 mm.
*Breadth.*—Approximately 12.4 mm.
Base:
*Shape.*—Slightly truncate.
Apex:
*Shape.*—Slightly depressed.
Pistil point: Obliquely positioned.
Skin:
*Thickness.*—Thin.
*Texture.*—Tender.
Tenacious to flesh: Yes.
Tendency to crack: Not observed in the dry season.
Color: Dark Red, (Plate 48, L-10, page 119).
Down:
*Quantity.*—Wanting.
Flesh color: Cardinal, (Plate 5, L-4, page 33).
Amygdalin:
*Quantity.*—Scant.
Juice production: Average as compared with other plum cultivars.
Flesh texture: Soft and melting at full commercial maturity.
Fibers:
*Numbers.*—Few.
*Texture.*—Fine and tender.
Ripening:
*Generally.*—Even.
Flavor: Delicate and considered subacid.
Aroma: Wanting.
Eating quality: Good.

STONE

Attachment: Semi-free; the subject variety adheres to the flesh over its entire surface.
Size:
*Generally.*—Small as compared with other plum cultivars.
*Average length.*—Approximately 18 mm.
*Average breadth.*—Approximately 16.1 mm.
*Average thickness.*—Approximately 9.7 mm.
Form:
*Generally.*—Oval.
Base:
*Position.*—Oblique.
Hilum:
*Shape.*—Narrow.
Apex:
*Shape.*—Rounded.
Sides:
*Generally.*—Equal and considered somewhat flattened.
Surface texture: Irregularly furrowed throughout.

Dorsal surface:

*Shape.*—Narrow.

Tendency to split: Not observed.

Color of Stone: Light brown, (Plate 11, B-6, Page 45).

Use: Fresh market-type plum.

Storage quality: Good.

Resistance to disease: Average as compared with other varieties.

Shipping qualities: Good.

Although the new variety of plum tree possesses the described characteristics when grown under the ecological conditions prevailing in Fresno, Calif., in the central part of the San Joaquin Valley of California, it is to be understood that variations of the usual magnitude and characteristics incident to changes in growing conditions, fertilization, pruning and pest control are to be expected.

Having thus described and illustrated my new variety of plum tree, what is new and desired to be secured by Letters Patent is:

1. A new and distinct variety of Plum Tree substantially as illustrated and described and which is somewhat similar to the Wuhl Plum tree (U.S. Plant Pat. No. 5,585) with which it is somewhat closely similar in its physical appearance, but from which it is distinguished therefrom and characterized principally as to novelty by bearing fruit which are ripe for commercial harvesting and shipment approximately May 27 through June 3 at Fresno, Calif. and which further produces a semi-freestone fruit which has a good flavor and an attractive skin coloration.

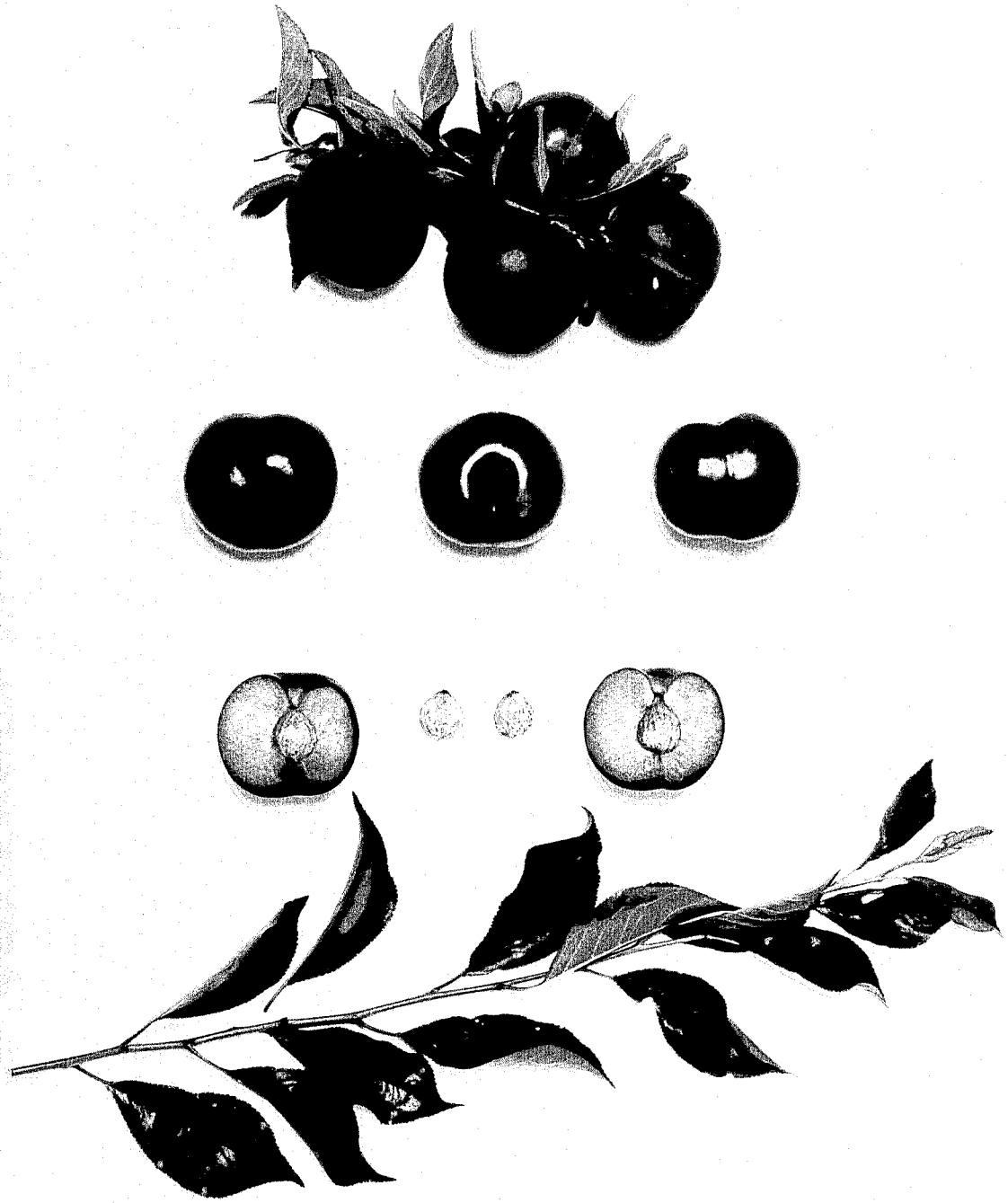

* * * * *